US010842958B1

(12) United States Patent
Rapoport

(10) Patent No.: US 10,842,958 B1
(45) Date of Patent: Nov. 24, 2020

(54) METHOD AND SYSTEM FOR DIAGNOSIS AND TREATMENT OF SLEEP DISORDERED BREATHING OF A PATIENT

(71) Applicant: New York University, New York, NY (US)

(72) Inventor: David M. Rapoport, New York, NY (US)

(73) Assignee: New York University, New York, NY (US)

( * ) Notice: Subject to any disclaimer, the term of this patent is extended or adjusted under 35 U.S.C. 154(b) by 886 days.

(21) Appl. No.: 14/972,596

(22) Filed: Dec. 17, 2015

Related U.S. Application Data

(60) Provisional application No. 62/096,419, filed on Dec. 23, 2014.

(51) Int. Cl.
*A61M 16/00* (2006.01)

(52) U.S. Cl.
CPC .... *A61M 16/0069* (2014.02); *A61M 16/0003* (2014.02); *A61M 2205/3327* (2013.01); *A61M 2205/3334* (2013.01)

(58) Field of Classification Search
CPC .......... A61M 16/0069; A61M 16/0051; A61M 16/0003; A61M 16/0021; A61M 16/022; A61M 16/0024
See application file for complete search history.

(56) References Cited

U.S. PATENT DOCUMENTS

| | | | | |
|---|---|---|---|---|
| 6,105,575 A * | 8/2000 | Estes | ................... | A61M 16/024 128/204.21 |
| 2004/0231670 A1* | 11/2004 | Bassin | .............. | A61M 16/0066 128/204.18 |
| 2008/0302364 A1* | 12/2008 | Garde | ............... | A61M 16/0045 128/204.23 |
| 2011/0166470 A1* | 7/2011 | Rapoport | ............. | A61B 5/0816 600/534 |
| 2013/0247914 A1* | 9/2013 | Truschel | ........... | A61M 16/0051 128/204.23 |
| 2017/0014588 A1* | 1/2017 | Truschel | ........... | A61M 16/1075 |

* cited by examiner

*Primary Examiner* — Margaret M Luarca
(74) *Attorney, Agent, or Firm* — Fay Kaplun & Marcin, LLP

(57) ABSTRACT

A system and method for providing ventilatory support to a patient suffering from sleep disordered breathing (SDB), in particular, non-obstructive SDB, such as Cheyne Stokes respiration and hypoventilation, including obesity hypoventilation syndrome. The system and method monitor obtain data corresponding to a breathing pattern of a patient and determine when the patient experiences oscillating breathing or low spontaneous ventilation. In particular, the system and method determine when the patient's real-time breathing patterns fall below a predetermined baseline threshold, and subsequently initiate a short series of mechanical breaths to be delivered to the patient.

12 Claims, 8 Drawing Sheets

METHOD AND SYSTEM FOR DIAGNOSIS AND TREATMENT OF SLEEP DISORDERED BREATHING OF A PATIENT

PRIORITY CLAIM

This application claims priority to U.S. Provisional Application Ser. No. 62/096,419 filed Dec. 23, 2014, the entire contends of which is hereby incorporated by reference herein.

FIELD OF INVENTION

The present invention relates generally to diagnosis and treatment of sleep disordered breathing, such as, for example, Cheyne-Stokes respiration and obesity hypoventilation syndrome in a patient.

BACKGROUND

Sleep disordered breathing (SDB) is a general group of disorders encompassing a number of different conditions that are characterized by irregular breathing, including intermittent disruptions to breathing patterns of a patient during sleep. For example, SDB may include a spectrum of respiratory disturbances ranging from irregular breathing patterns, periodic respiration, shallow breathing to reduced airflow (hypopnea, flow limitation, and snoring) or total absence of airflow (apnea), despite continued respiratory efforts by the patient. The pathophysiologies of SDBs are believed to be vastly different from each other and are not all fully understood. However, it is believed that different types of SDB may be generally categorized to groups of conditions representing ventilatory instabilities caused by abnormal breathing control by the brain and/or structural instabilities in the patient's airway, particularly upper airway.

One of the most common types of SDB is obstructive sleep apnea/hypopnea syndrome (OSAHS), which is a well-recognized disorder that may affect as much as 1-5% of the adult population. OSAHS is associated with conditions in which there is anatomic or functional narrowing of the patient's upper airway, and is characterized by an intermittent obstruction of the upper airway occurring during sleep. In a patient suffering from OSAHS, the patient may experience partial or complete airway collapse. This can occur associated with the loss of airway tone which is characteristic of the onset of sleep and which may be exaggerated in OSAHS. Since 1981, positive airway pressure (PAP) applied by a tight fitting nasal mask worn during sleep has evolved as the most effective treatment for OSAHS, and is now the standard of care. The availability of this non-invasive form of therapy has resulted in extensive publicity for sleep apnea/hypopnea and the appearance of large numbers of patients who previously may have avoided the medical establishment because of the fear of tracheostomy. Increasing the comfort of the system (e.g., by minimizing the applied nasal pressure) has been a major goal of research aimed at improving patient compliance with therapy. PAP therapy is directed to maintaining pressure in the collapsible portion of the airway at or above the critical "tissue pressure" at all times. In conventional CPAP, this is achieved by raising the airway pressure in the entire respiratory system to a level higher than this critical pressure.

There is increasing awareness of other types of SDB caused by non-obstructive respiratory abnormalities. For example, non-obstructive types of SDB may include Cheyne-Stokes respiration (CSR), hypercapnic hypoventilation, obesity hypoventilation syndrome (OHS), central sleep apnea, central hypopneas, etc. Cheyne Stokes respiration (CSR) is a pattern of waxing/waning respiration seen mostly in sleep and defined by periods of central apnea that produce significant $O_2$ desaturation, alternating with hyperventilation and arousal from sleep at the peak of breathing, associated with sympathetic over-activation. CSR is seen in up to 50% of patients with congestive heart failure (CHF) and is associated with increased mortality. Hypoventilation may be characterized by an increase in a partial pressure of $CO_2$ ($PCO_2$) caused by either reduced minute ventilation and/or increased ventilatory deadspace. Sleep hypoventilation is accentuated in disease states with potential carryover to the daytime, producing chronic hypercapnia during wakefulness due to failure of compensation during sleep and/or during wakefulness. Elevation of blood bicarbonate concentration, although appropriate to defend blood pH, provides a mechanism for perpetuation of a chronic hypercapnic state caused by blunting of respiratory drive. OHS is a specific form of hypoventilation in obese patients suffering from chronic daytime hypercapnia.

Conventional PAP therapy has been less successful in the treatment of non-obstructive SDB as compared to OSAHS. The applied pressure is either a constant pressure, or a pressure based on breath-by-breath determination of the need for treatment. Administration of a constant pressure is not suitable for patients suffering from irregular, e.g., oscillating, breathing patterns, because constant pressure primarily addresses airway obstruction and does little to modify the level of breathing. To accomplish changes in the amount of breathing, devices that deliver a larger pressure only during inspiration (i.e., in a bi-level PAP or pressure support) have been developed to assist the patient in developing breathing efforts. The devices that apply assisted bi-level pressures are either based on a constant assistance, or a level that changes with time. During periods where the patient is providing low levels of breathing effort, however, constant bi-level pressures may be insufficient, and during periods where the patient is providing high levels of breathing effort, the constant bilevel pressures may be excessive and cause discomfort to the patient. It is also difficult to apply bi-level pressures that are based on rapidly changing breath-by-breath determination of the need for treatment. In particular, conventional PAP devices may impart an intrinsic resistance or may not be sufficiently sealed such that pressure and/or airflow dissipates and/or leaks from the device. Therefore, these additional factors make it difficult to accurately measure the exact amount of a patient's breathing, and thus limit the complex algorithms currently in use when bi-level PAP is varied from a set fixed pattern with every breath.

Moreover, the physician is often unable to identify the primary cause of non-obstructive SDB in a patient prior to administering any type of treatment. However, different types of non-obstructive SDB (e.g., CSR, hypercapnic hypoventilation, and OHS) may require different types of treatment regiments. The pathophysiology of a particular patient's condition can often only be identified empirically. Thus, a physician cannot select an appropriate treatment without knowledge of the primary cause of SDB in the patient. Therefore, patients suffering from non-obstructive SDB must be first diagnosed with a specific type of SDB (e.g., CSR, hypercapnic hypoventilation, or OHS) before an appropriate treatment regiment can be administered. In particular, a diagnostic study needs to be performed before administering any type of treatment. This diagnosis may include a sleep study in a laboratory, is often tedious and time consuming, and delays administration of the much-needed treatment to the patient.

Therefore, there is a continuing need in the art for an improved device and method for treating SDB, particularly non-obstructive SDB characterized by periodically varying and irregular breathing patterns. It is an object of the present invention to provide a system and method for treating non-obstructive SDB that provides sufficient ventilatory support without excess pressure causing discomfort to the patient. It is also an object of the present invention to provide a system and method that determines a primary cause of SDB (e.g., CSR, hypercapnic hypoventilation, or OHS) and selects the appropriate treatment regiment in response.

SUMMARY OF THE INVENTION

In accordance with the foregoing objectives and others, one embodiment of the present invention provides systems and methods for providing intermittent ventilatory support. First, the method comprises a step for obtaining data corresponding to a breathing pattern of a patient. Next, the method determines when the breathing pattern of the patient falls below a predetermined threshold, or when the appearance of apneas indicates the onset of sleep, which is the state when sleep disordered breathing occurs. The method further comprises the step for supplying an airflow to an airway of the patient in a predetermined pattern when the breathing pattern falls below the predetermined threshold. The predetermined pattern corresponds to a short series of mechanical breaths or a fundamental change in the pattern of ventilator support to be provided.

In one aspect, an alternative method for providing intermittent ventilatory support is provided. First, the method comprises a step for obtaining data corresponding to a breathing pattern of a patient. Next, the method determines a state of wakefulness of the patient based on the breathing pattern. The method further comprises the step for supplying an airflow to an airway of the patient in a predetermined pattern when the state of wakefulness is a sleep state. The predetermined pattern corresponds to a short series of mechanical breaths.

In another aspect, a method for treating hypercapnia is provided. The method comprises a step for obtaining data corresponding to a spontaneous breathing pattern of a patient in an awake state. Next, the method monitors a real-time breathing pattern of the patient, and determines when the real-time breathing pattern of the patient falls below a predetermined threshold or otherwise suggests the onset of sleep. The exact value of the level of ventilation is not needed, as it is not used to determine the exact response to a real-time breathing pattern falling below a predetermined threshold, only to trigger a subsequent step in response to the breathing pattern falling below the predetermined threshold. When the real-time breathing pattern falls below the predetermined threshold, the method further comprises the step for supplying an airflow to an airway of the patient at a rate or a pressure such that the patient will be forced to breath at a rate or a volume greater than or equal to a rate or a volume of the spontaneous breathing pattern of the patient. When the patient then increases his breathing or otherwise indicates a state of wakefulness has recurred, the forced breathing may be discontinued (as hypoventilation patients when awake usually breathe sufficiently).

In a further aspect, a method for treating oscillating breathing is provided. The method comprises a step for obtaining data corresponding to a breathing pattern of a patient. Next, the method determines when the breathing pattern of the patient falls below a predetermined threshold, as a trigger for further action. The method further comprises the step for supplying an airflow to an airway of the patient in a predetermined pattern when the breathing pattern falls below the predetermined threshold. The predetermined pattern corresponds to a short series of mechanical breaths. The method further comprises the step of discontinuing the airflow to the airway of the patient.

These and other aspects of the invention will become apparent to those skilled in the art after a reading of the following detailed description of the invention, including the figures and appended claims.

DETAILED DESCRIPTION

Figure 1:
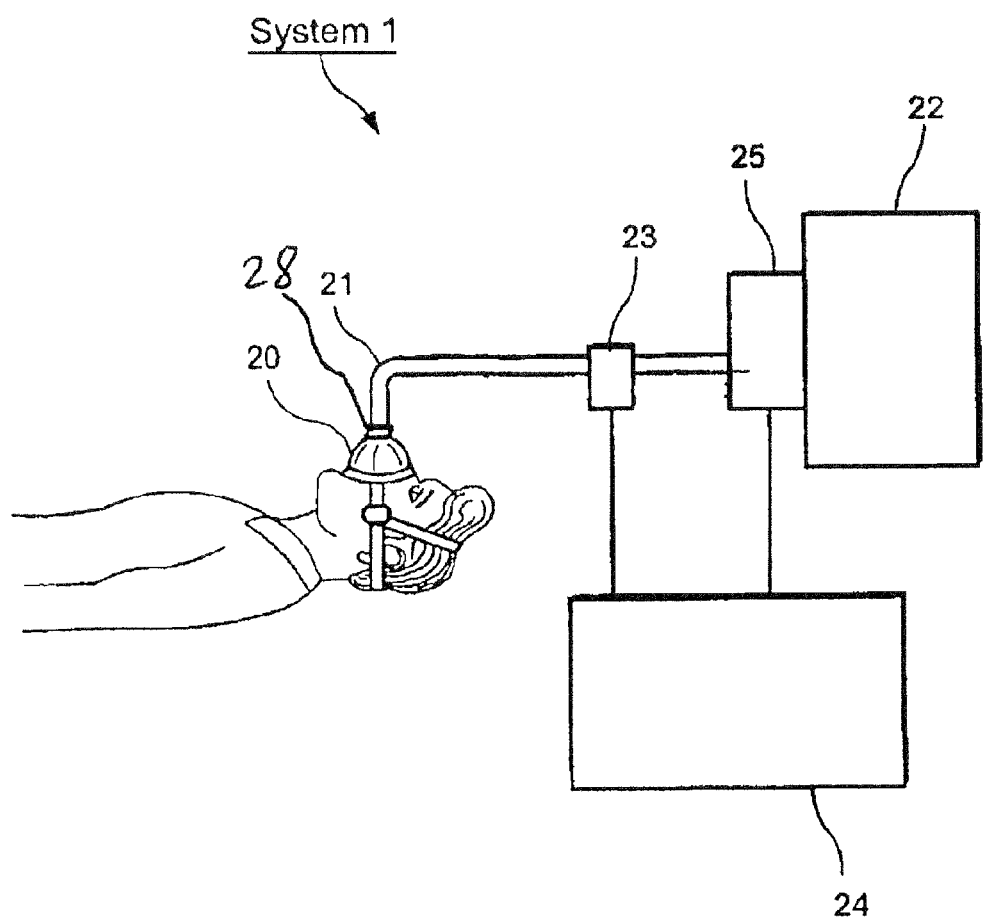
FIG. 1 shows an exemplary embodiment of a system for treatment of SDB according to the present invention.

As discussed above, delivery of a constant level bi-level pressure to a patient may be insufficient during low levels of breathing effort, and that it is difficult to apply bi-level pressures that are based on rapidly changing breath-by-breath determination of the need for treatment. However, more general information such as the gross pattern of breathing may be readily detected and can be used for real-time determination of application treatment pressures. The exemplary embodiments provide systems and methods for diagnosis and treatment of SDB, more particularly non-obstructive SDB, such as for, example, CSR, hypercapnic hypoventilation, and OHS in a patient. For example, the systems and methods of the exemplary embodiments provide intermittent ventilatory support to a patient suffering from non-obstructive SDB characterized by irregular breathing patterns or insufficient breathing such that adequate breathing, either spontaneously by the patient or via assisted ventilatory support, occurs without noticeable discomfort that wakes the patient from sleep. In addition, the exemplary embodiments may also include a diagnostic method for determining whether a patient is suffering from CSR or OHS. An appropriate treatment may be selected in response to the diagnosis. The exemplary embodiments may be further understood with reference to the following description of exemplary embodiments and the related appended drawings, wherein like elements are provided with the same reference numerals.

FIG. 1 shows an exemplary embodiment of a system 1 according to the present invention. The system 1 may include a mask 20 connected via a tube 21 to receive airflow from a flow generator 22. The mask 20 may be configured to cover a patient's nose and/or mouth. Sensors 23 may be coupled to the flow generator 22 to detect the rate of airflow to/from the patient and/or a pressure supplied to the patient by the flow generator 22. In an alternative exemplary embodiment, the sensors 23 may position within or near the mask to detect the rate of airflow to/from the patient and/or a pressure supplied to the patient by the flow generator 22.

Signals corresponding to the airflow and/or the pressure are provided to a processing arrangement 24 for further analysis and/or processing. Those skilled in the art will understand that the exemplary embodiments for the processing arrangement 24 described herein may be implemented in any number of manners, including as a separate software module, as a combination of hardware and software, etc. For example, the exemplary treatment methods may be embodiment in one or more programs stored in a non-transitory storage medium and containing lines of code that, when compiled, may be executed by at least one of the plurality of processor cores or a separate processor. In some embodiments, the processing arrangement 24 comprises a plurality of processor cores and a set of instructions executing on the plurality of processor cores may be provided. The set of instructions may be operable to perform the exemplary methods discussed below.

The processing arrangement 24 outputs a signal to a flow control device 25 to control an airflow and/or pressure applied to the flow tube 21 by the flow generator 22. Those skilled in the art will understand that, for certain types of flow generators which may by employed as the flow generator 22, the processing arrangement 24 may directly control the flow generator 22, instead of controlling flow therefrom by manipulating a separate flow control device 25. The system 1 may optionally include a continuously leaking port or a venting arrangement 28 coupled to the mask 20. The venting arrangement 28, for example, may include a valve mounted in an opening located, for example, on or near the mask 20 as shown in FIG. 1. The venting arrangement 28 allows for gases contained in the exhaled airflow of the patient to be diverted to ambient from the incoming airflow to prevent re-breathing of the exhaled gases.

Figure 2:
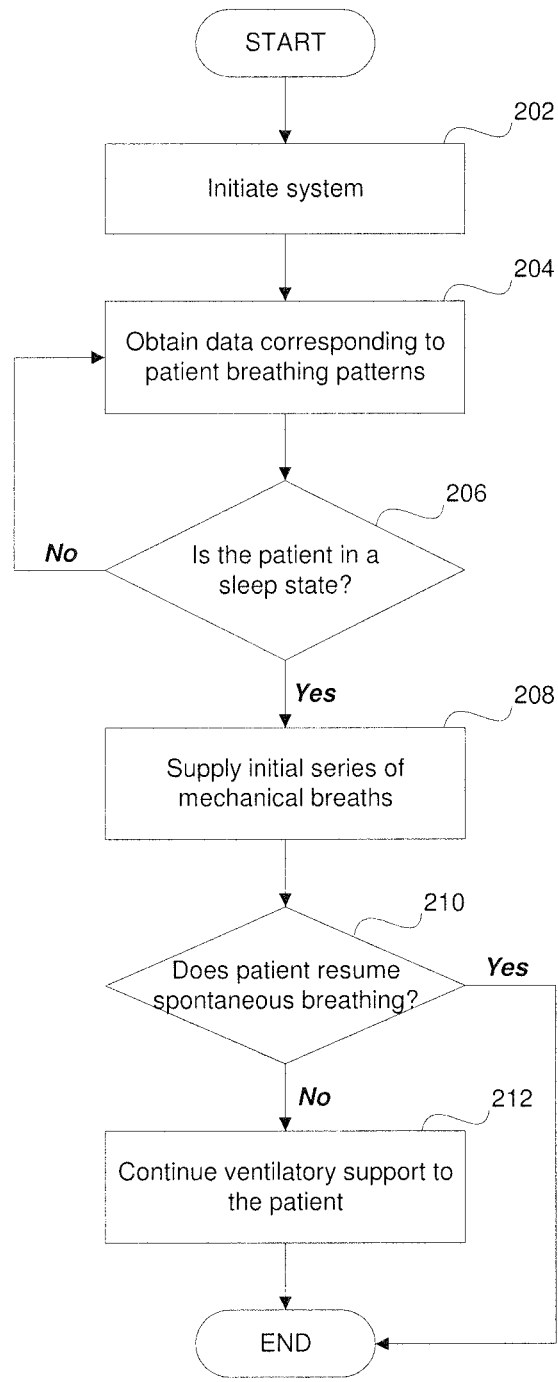
FIG. 2 shows an exemplary embodiment of a method for treatment of SDB according to the present invention.

FIG. 2 illustrates an exemplary method 200 for treating a patient with non-obstructive SDB. The method 200 described herein provides a general method for initiating mechanical breathing and selecting an appropriate treatment regimen based on the patient's response to the initial mechanical breaths. The method 200 will be described with reference to the exemplary system 1 of FIG. 1; however, those of skill in the art will understand this is only exemplary and that the method 200 may be implanted by various other systems as well. The method 200 begins with step 202, where system 1 is initiated and the mask 20 is placed over the patient's nose and/or mouth. The system 1 may be initiated by any suitable means for setting up a ventilatory support system for supplying airflow and detecting the patient's breathing patterns. For example, the system 1 may be initialized to receive a number of pre-set settings, including a pre-set predetermine threshold level, and a pre-set predetermined pattern, as further discussed below. In some embodiments, step 202 may also include a titration procedure for determining the maximum amount of pressure that can be delivered to a patient without waking the patient from sleep. The titration procedure may be conducted using a number of suitable methods. For example, to determine the maximum amount of pressure that can be delivered to a patient without waking the patient from sleep, the patient may undergo multiple attempts to provide increasingly larger pressures during the periods of ventilation. The pressure level that produces an arousal (i.e., wakes the patient from sleep) would determine an excessive pressure that should not be used. Thus, the evaluation may be repeated at a lower pressure until a suitable pressure is reached. This repeated evaluation could be based on either an in-laboratory period of observation by a technician, or based on automated recognition of an arousal from the irregular breathing pattern that occurs concurrently with waking of the patient from sleep (as opposed to suppression of breathing in OHS, or regular but increasing ventilation that occurs in CSR after a period of hypoventilation). Other non-limiting examples of suitable methods and devices for a titration procedure are described in PCT Application Publication No. WO2014/150227, the disclosures of which are hereby incorporated by reference in their entirety.

In step 204, the sensors 23 and the processing arrangement 24 monitors the patient's breathing patterns, preferably in real-time, and obtains data corresponding to the patient's instantaneous or near-instantaneous breathing patterns. Specifically, the sensors 23 may collect data corresponding to the patient's breathing patterns and provide the data to the processing arrangement 24. The processing arrangement 24 may store the data provided by the sensors 23 for subsequent analysis.

In step 206, the processing arrangement 24 analyzes the data provided by the sensors 23 and may utilize previously stored patient data along with real-time data provided by the sensors 23 to determine a current state of wakefulness of the patient (e.g., whether the patient is asleep, awake and breathing regularly or awake and breathing irregularly due to distress or anxiousness). Such a determination can be made using a number of suitable methods. Non-limiting examples of suitable methods and devices for detecting a current state of wakefulness of the patient, e.g., whether a user is in a sleep or awake state, are described in U.S. Pat. No. 7,896,812, the disclosures of which are hereby incorporated by reference in their entirety. Other exemplary apparatus for detecting the sleep or awake states of the patient include the SensAwake™ technology currently incorporated in the Fisher & Paykel Healthcare ICON™+ device(s). However, any suitable device or method for detecting sleep and awake states of a patient may be used. If the patient transitions from an awake state to a sleep state, the method 200 proceeds to step 208.

In step 208, the system 1 administers an initial series of mechanical breaths to the patient. For example, the processing arrangement 24 directs the flow control device 25 and/or flow generator 22 to supply airflow in accordance with a predetermined pattern corresponding to a short series of mechanical breaths, such as in bi-level PAP therapy. The predetermined pattern can be pre-set by the user, such as a physician or the patient, and preferably, is determined independently from the breathing patterns measured by sensors 23. This pre-set pattern may be entered by the user, either manually inputted or electronically transmitted to the system 1 or processing arrangement 24 from another device, before or during the initialization step (step 202). In an alternative embodiment, the predetermined threshold may be a default pre-set pattern that is stored within the processing arrangement 24. In one particular exemplary embodiment, the predetermined pattern may correspond to a short series of three to five breaths. In some embodiments, the predetermined pattern may include a series of breaths having equal amplitudes, e.g., the breaths having the same peak rate, pressure, frequency and/or tidal volume levels. In other embodiment, the predetermined pattern may include a series of breaths having a smaller first breath with the remainder having equal amplitudes. In a further embodiment, the predetermined pattern may include a series of breaths having increasing amplitude, e.g., the breaths having increasing peak rate, pressure, frequency and/tidal volume levels, so that the initial airflow delivered to the patient is smaller, and thereby reducing the risk of discomfort and waking the patient from sleep. In one exemplary embodiment, the predetermined pattern may include a series of breaths corresponding to the maximum level of breathing (e.g., breathing patterns, pressure, rate, ventilation, respiratory frequency and/or tidal volume) that can be delivered to a patient without waking the patient from sleep, as determined by the titration procedure described in step 202. In another exemplary embodiment, the predetermined pattern may include a series of breaths at a level of breathing (e.g., breathing patterns, pressure, rate, ventilation, respiratory frequency and/or tidal volume) corresponding to or less than that provided by the patient's own spontaneous breathing in an awake state. In a further exemplary embodiment, the predetermined pattern may include a series of breaths at a level of breathing (e.g., breathing patterns, pressure, rate, ventilation, respiratory frequency and/or tidal volume) is greater than or equal to that provided by the patient's own spontaneous breathing in an awake state.

In some embodiments, the mechanical breaths may be set to a predetermined pattern that corresponds to a bi-level PAP for a short series of breaths. In bi-level PAP, a first pressure is set as an inspiratory pressure or IPAP and a second lower pressure is set as an expiratory pressure or EPAP. In one particular embodiment, the inspiratory pressure may be set based on the maximum amount of pressure that can be delivered to a patient without waking the patient from sleep, as determined by the titration procedure described in step 202. In another embodiment, the inspiratory pressure may be set corresponding to or less than that provided by the patient's own spontaneous breathing in an awake state. In a further embodiment, the inspiratory pressure may be set greater than or equal to that provided by the patient's own spontaneous breathing in an awake state. Typically, the inspiratory pressure may be set from 10 to about 30 cm of $H_2O$, or from 15 to about 25 cm of $H_2O$. The lower expiratory pressure may be set from 0 to about 20 cm of $H_2O$, from 0 to about 15 cm of $H_2O$, from 0 to about 5 cm of $H_2O$, or from about 5 cm to about 15 cm of $H_2O$. In some embodiments, the differential ($\Delta P$) between the lower expiratory pressure and the inspiratory pressure is a difference of about 10 to about 25 cm of $H_2O$, about 15 to about 25 cm of $H_2O$, or about 25 cm of $H_2O$.

In some alternative embodiments, the method 200 continues to monitor the breathing patterns of the patient while administering the initial series of mechanical breaths to the patient in accordance with step 208. If the processing arrangement detects that the patient is woken by any one of the initial series of mechanical breaths, the method 200 is aborted. Alternatively, if the patient spontaneously takes a large irregular breath, the method 200 may also be aborted. In some embodiments, when the method 200 is aborted, the flow generator 22 may stop delivery of any airflow to the patient. In another embodiment, the flow generator 22 may provide a low pressure at a comfortable level to the patient when aborting the method 200.

In step 210, after delivery of the initial series of mechanical breaths to the patient, the processing arrangement 24 continues to monitor the breathing patterns of the patient via the sensors 23 and determine if the patient has resumed spontaneous breathing based on his own effort, with or without ventilatory assistance from the flow generator 22. In some types of SDB (e.g., oscillating breathing, CSR), the initial series of mechanical breaths is sufficient to return the patient's spontaneous breathing to normal patterns. In that case, no additional therapeutic airflow from the flow generator 22 is needed. The method 200 may optionally continue to monitor the patient's breathing patterns to determine if the patient transitions from a sleep state to an awake state. If the patient is awake, ventilatory support is no longer supplied to the patient.

In other types of SDB (e.g., hypercapnic hypoventilation, OHS), the initial series of mechanical breaths may trigger the patient to further reduce his own spontaneous breathing, and this indicates that patient has abandoned control of his level of breathing to the mechanical ventilatory support (i.e., has become "controlled" by the ventilatory support). The patient will therefore be provided with ventilatory support from the flow generator 22, and ventilation in excess of his demand, which promotes rectification of hypercapnic hypoventilation. If the patient does not resume spontaneous breathing or experiences reduced spontaneous breathing, the method 200 proceeds to step 212 to further administer airflow to the patient until the patient resumes spontaneous breathing on his own, typically when the patient is woken from sleep, at which time the assistance in ventilation is discontinued and the patient is allowed to control his own spontaneous breathing. For example, in step 212, the processing arrangement 24 may direct the flow control device 25 and the flow generator 22 to continue to administer breaths to the patient in accordance with the same predetermined pattern as used in step 208. Alternatively, the processing arrangement 24 may direct the flow control device 25 and the flow generator 22 to continue to administer breaths to the patient at the maximum amplitude selected by the predetermined pattern of step 208 until the patient's spontaneous pattern indicates he is awake. In another embodiment, the processing arrangement 24 may incrementally increase the amplitude of the breaths administered to the patient. In one exemplary embodiment, the processing arrangement 24 may incrementally increase the amplitude of the breaths administered to the patient until it reaches the maximum amount of pressure that can be delivered to a patient without waking the patient from sleep, as determined by the titration procedure described in step 202. In another exemplary embodiment, the processing arrangement 24 may increase the amplitude of the breaths administered to the patient to a level greater than that provided by the patient's own spontaneous breathing in an awake state.

In an alternative embodiment, step 210 may also be used to diagnose the type of SDB experienced by the patient. Based on the patient's response to the initial series of mechanical breaths to the patient, a primary cause of SDB may be diagnosed. If the patient resumes regular spontaneous breathing based on his own efforts, the patient may be diagnosed with oscillating breathing or CSR. If the patient does not resume spontaneous breathing based on his own efforts, the patient may be diagnosed with hypercapnic hypoventilation or OHS. More particularly, if the patient resumes irregular spontaneous breathing, it is determined that he has awoken and all forms of ventilatory assistance are reduced or removed.

Figure 3:
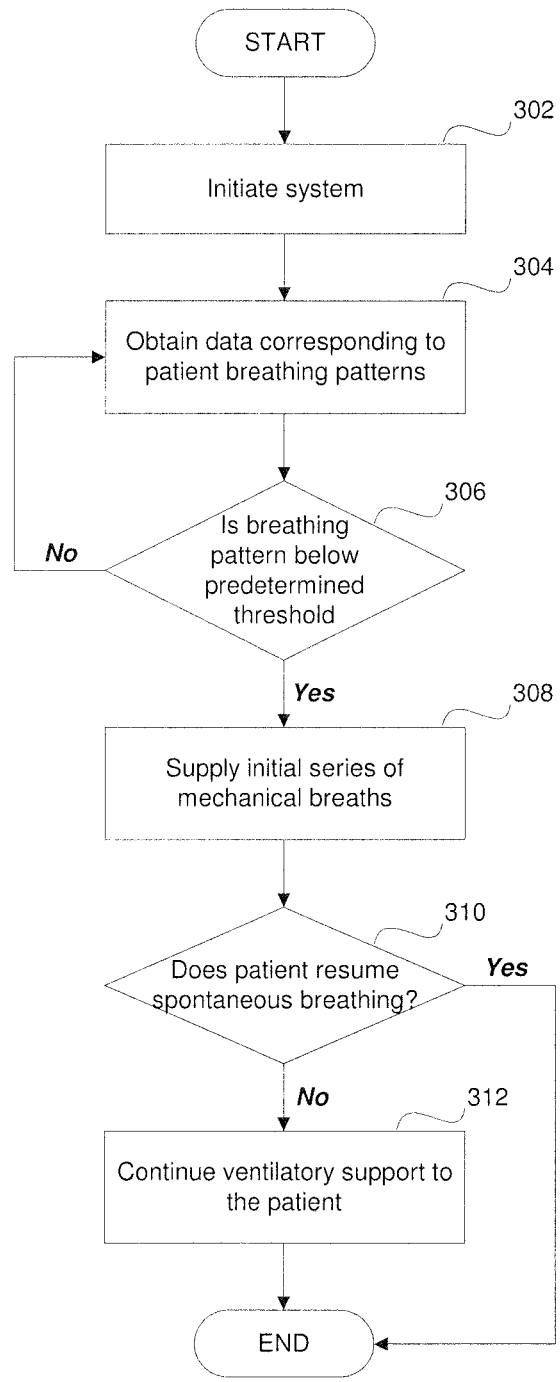
FIG. 3 shows an alternative exemplary embodiment of a method for treatment of SDB according to the present invention.

FIG. 3 illustrates another exemplary method 300 for treating a patient with non-obstructive SDB. This method 300 is substantially similar to that described above with reference to FIG. 2. However, steps 306 and 310 are notably different from steps 206 and 210. The method 300 described herein provides an alternative method for initiating mechanical breathing and selecting an appropriate treatment regimen based on the patient's response. The method 300 will be described with reference to the exemplary system 1 of FIG. 1; however, those of skill in the art will understand this is only exemplary and that the method 300 may be implanted by various other systems as well.

The method 300 begins with steps 302 and 304, which correspond to steps 202 and 204 described above with reference to method 200. In step 306, the processing arrangement 24 analyzes the data provided by the sensors 23 and may utilize previously stored patient data along with real-time data provided by the sensors 23 to determine if the patient's breathing pattern has fallen below a predetermined threshold. The analysis of step 306 may be based on data collected by the sensors 23 for a single breath, or may be determined using data stored in the processing arrangement collected by the sensors 23 over a plurality of breaths, for example, over the most recent 5 breaths, over the most recent 3 breaths, or over the most recent 2 breaths. The processing arrangement 24 may determine a baseline for the patient's breathing patterns, pressure, rate, ventilation, respiratory frequency and/or tidal volume and establish a predetermined threshold level. For example, the predetermined threshold may be a percentage of the baseline, such as, for example, 90%, 80%, 70%, 60%, or 50% of the initial baseline breathing pattern, pressure, rate ventilation, respiratory frequency and/or tidal volume. In certain embodiments, the predetermined threshold may be a pre-set proportion of the patient's immediately preceding baseline breathing pattern, pressure, rate ventilation, respiratory frequency and/or tidal volume (e.g., 30%, 50% or 70% of the preceding baseline). In another embodiment, the predetermined threshold may be a pre-set value for the patient's breathing pattern, pressure, rate, ventilation, respiratory frequency and/or tidal volume, as determined by the user, such as a physician or the patient. This pre-set value may be entered by the user, either manually inputted or electronically transmitted to the system 1 from another device, before or during the initialization step (step 302). In an alternative embodiment, the predetermined threshold may be a default pre-set value that is stored within the processing arrangement 24. If the processing arrangement 24 determines that the real-time data provided by the sensors 23 show a breathing pattern that is above the predetermined threshold, the method 300 continues to monitor the patient and returns to step 304. If the processing arrangement 24 determines that the real-time data provided by the sensors 23 show a breathing pattern that falls below the predetermined threshold, the method 300 continues to step 308. Step 308 corresponds to step 208, as described above with reference to method 200.

In step 310, after the delivery of the initial series of mechanical breaths to the patient, the processing arrangement 24 continues to monitor the breathing patterns of the patient via sensors 23 and determine if the patient has resumed spontaneous breathing based on his own effort, without ventilatory assistance from the flow generator 22. In some types of SDB (e.g., CSR), the initial series of mechanical breaths is sufficient to return the patient's spontaneous breathing to normal patterns. In that case, no additional airflow from the flow generator 22 is needed. The method 300 may optionally continue to monitor the patient's breathing patterns to determine if the patient resumes irregular or oscillating breathing, such as CSR. For example, the method 300 may continue to monitor the patient's breathing patterns to determine if the patient's breathing pattern falls below a predetermined threshold, in the same manner as describe in step 306. If the patient's breathing pattern falls below the predetermined threshold, the method 300 returns to step 308 for administration of an additional series of mechanical breaths to the patient. In other embodiments, the initial series of mechanical breaths are withheld after the first recurrence of irregular or oscillating breathing, more particularly, after the first recurrence of the patient's breathing pattern falling below the predetermined threshold. However, if the patient resumes irregular or oscillating breathing, such as CSR, more than once, or if the patient's breathing pattern falls below the predetermined threshold more than once, the method 300 returns to step 308 for administration of an additional series of mechanical breaths to the patient.

In other types of SDB (e.g., OHS), the initial series of mechanical breaths triggers the patient to reduce his own spontaneous breathing further, and this signals that the patient will cede control to the mechanical ventilator and may require further ventilatory support from the flow generator 22. If the patient does not resume spontaneous breathing or experiences reduced spontaneous breathing, the method 300 proceeds to step 312 to further administer airflow to the patient corresponding to a level of breathing that may be higher than that the patient would breathe on his own, even while awake, but allows the ventilator to deliver to this higher level until the patient resumes spontaneous breathing on his own, generally upon awakening of the patient. Step 312 corresponds to step 212, as described above with reference to method 200.

Figure 4:
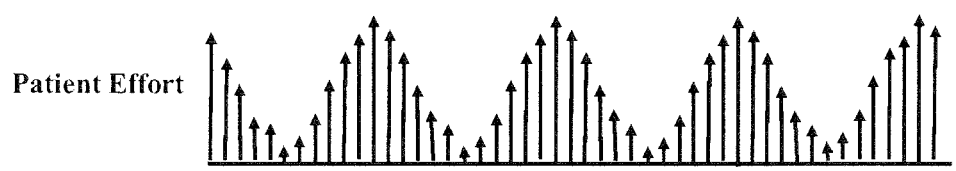
FIG. 4 shows an exemplary breathing pattern of a patient having oscillating ventilation patterns.
Figure 5:
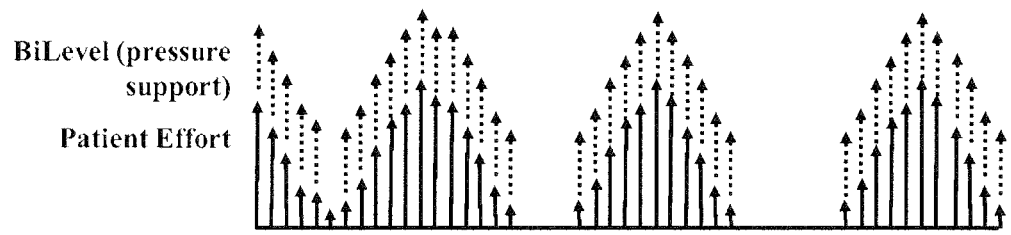
FIG. 5 shows an exemplary breathing pattern of a patient having oscillating ventilation patterns administered with bi-level ventilatory assistance at a constant pressure.

The above-described methods 200 and 300 may be used for diagnosing and/or treating patients' irregular or oscillating breathing patterns. Patients suffering from irregular or oscillating breathing patterns, such as CSR, have sufficient ventilation, but experience breathing instability that result in oscillating patterns. FIG. 4 illustrates an exemplary breathing pattern of a patient having oscillating ventilation patterns. The solid lines represent the patient's own breathing efforts. One key identifying feature of these types of patients is that the arterial partial pressure of $CO_2$ ($PCO_2$) while awake, and the patient's serum bicarbonate levels are normal. However, the patient experiences oscillating levels of breathing. Although the oscillations may affect the upper airway (producing obstructive as well central hypopnea), the primary object of ventilatory assistance devices is to stabilize the pattern, rather than augment the overall respiration. For patients suffering from irregular or oscillating breathing patterns, particularly CSR, a constant administration of ventilatory support, e.g., continuous delivery of bi-level ventilatory assistance at a constant pressure, as show in FIG. 5, cannot stabilize the CSR. The solid lines in FIG. 5 represent the patient's own breathing efforts and the dotted lines represent airflow provided by bi-level ventilatory support. As can be seen, such ventilatory assistance magnifies instead of damping the oscillations.

Figure 6:
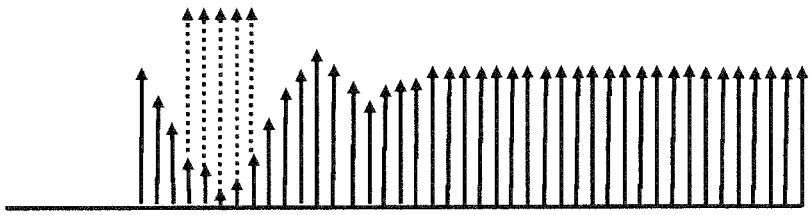
FIG. 6 shows an exemplary breathing pattern of a patient having oscillating ventilation patterns administered with a short series of mechanical breaths.

The methods 200 and 300 as described above deliver an initial series of mechanical breaths. It is believed that this initial series of mechanical breaths administered in step 208 or 308 act like a single pulse intervention that dampens the irregular or oscillating breathing patterns of the patient, as illustrated in FIG. 6, without the need to provide further ventilatory support. The solid lines in FIG. 6 represent the patient's own breathing efforts and the dotted lines represent airflow administered by the initial series of mechanical breaths. This pulse-like approach does not require precise monitoring and detection of the patient's instantaneous breathing volume, but instead, relative increases and/or decreases in patient breathing and/or ventilation are sufficient to trigger administration of the initial series of mechanical breaths. For example, method 300 does not require precise detection of the patient's breathing patterns, but instead triggers step 308 upon detection of the patient's breathing level falling below a predetermined threshold value (step 306). The pulse may be a predetermined series of mechanical breaths that are independent of the patient's breathing patterns. It is believed that the reduction in monitoring and detection of real-time breathing patterns provide a major improvement to treatment of irregular or oscillating breathing (e.g., CSR), as such real-time measurements provide computationally complex challenges and accurate measurements are difficult to obtain.

Figure 7:
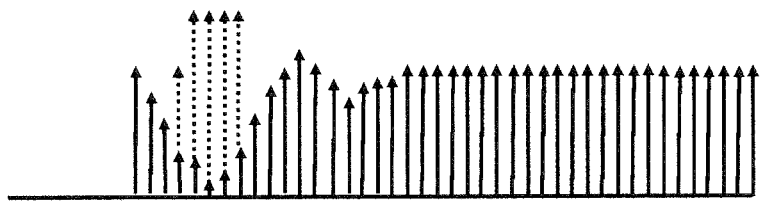
FIG. 7 shows an exemplary breathing pattern of a patient having oscillating ventilation patterns administered with a short series of mechanical breaths, wherein the first of which is lower in amplitude than the other breaths.
Figure 8:
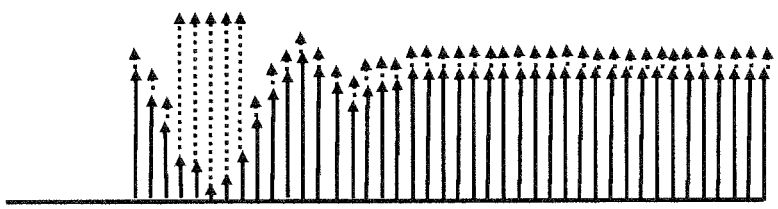
FIG. 8 shows an exemplary breathing pattern of a patient having oscillating ventilation patterns administered with a short series of mechanical breaths in combination with continuous positive air pressure (CPAP) therapy.

The initial series of mechanical breaths may be administered according to any predetermined pattern. For example, the predetermined pattern may be a series of breaths having equal amplitudes. In other embodiments, the first of the series of breaths may have a lower amplitude so as to reduce the risk of causing discomfort and awakening the patient from sleep. FIG. 7 illustrates an example of a patient having oscillating ventilation patterns administered with a short series of breaths, the first of which is lower in amplitude than the other breaths. The solid lines in FIG. 7 represent the patient's own breathing efforts and the dotted lines represent airflow administered by the short series of mechanical breaths. In another embodiment, the initial series of breaths may be used in combination with delivery of a CPAP therapy to overcome physical obstructions in the patient's airway. FIG. 8 illustrates an example of a patient having oscillating ventilation patterns administered with a short series of breaths in combination with CPAP therapy. The solid lines in FIG. 8 represent the patient's own breathing efforts and the dotted lines represent airflow administered by the short series of mechanical breaths. In a further embodiment, the initial series of breaths may be used in combination with delivery of a minimum bi-level PAP therapy to improve patient comfort.

Figure 9:
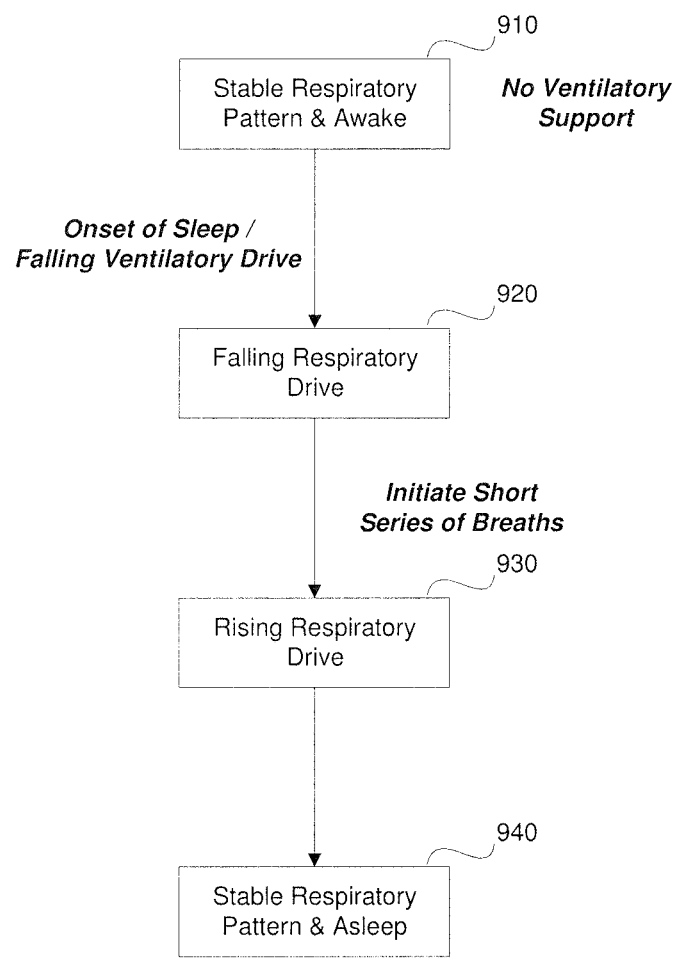
FIG. 9 shows an exemplary progression of breathing states for a patient having oscillating ventilation patterns administered with a short series of mechanical breaths.

FIG. 9 illustrates an exemplary progression of a patient's breathing states during periodic, falling or oscillating breathing that appears with sleep, and as the patient's breathing is treated with ventilatory support in the manner described above in methods 200 and 300. In state 910, the patient is awake and demonstrates a respiratory pattern with relatively high ventilatory drive, which may be stable and regular but often has additional irregularities. Typically, the patient in state 910 has a high respiratory rate but experiences irregularities in breathing rate and tidal volume. The patient in state 910 typically does not receive any ventilatory support. As the patient falls asleep, the onset of sleep transitions the patient from state 910 to state 920. In state 920, the patient may experience a falling respiratory drive. In patients suffering from CSR, irregularities and oscillations in breathing patterns is particularly pronounced during onset of sleep. The patient in state 920 typically experiences a falling respiratory rate and a falling respiratory drive. Step 306, as described above, determines if the patient's breathing pattern has fallen below a predetermined threshold during such a pattern. It is believed that step 306 may be utilized to detect the patient's transition from state 910 to state 920 and thus, trigger ventilatory support for a patient undergoing CSR. For example, the processing arrangement 24 may direct the flow generator 22 to administer an initial series of mechanical breaths to the patient, as described above in steps 208 and 308. It is believed that this initial series of mechanical breaths administered in step 208 or 308 dampens the oscillating breathing patterns and restores patient breathing to a stable respiratory pattern with relatively high ventilatory drive (state 940) without waking the patient from sleep. Therefore, airflow to the patient may be discontinued after the initial series of mechanical breaths.

The above-described methods 200 and 300 can be used for diagnosing and/or treating patients having hypercapnic hypoventilation, including OHS. Patients suffering from hypoventilation overall have insufficient ventilation to excrete their excess $CO_2$, and thus one key identifying feature of these patients is that the arterial partial pressure of $CO_2$ ($PCO_2$) while the patient is awake, along with the patient's serum bicarbonate levels are elevated. Typically, patients suffering from hypoventilation experience inadequate amount of breathing (e.g., inadequate breathing rate or inspiratory volume by the patient). Hypoventilation is also often associated with a further drop in ventilatory drive that occurs as the patient transitions from an awake state to a sleep state.

When the patient is in an awake state, the rate and/or pressure of any ventilatory support administered to the patient can be set lower than the breathing levels of the patient's own spontaneous breaths so as to avoid discomfort. During wakefulness, the assisted ventilation may not be sufficient to decrease drive fully and suppress breathing efforts. Patient's own spontaneous breathing efforts, which suffers from low ventilation, are resumed in an awake state. While asleep, the patient's spontaneous breathing efforts can be supplemented with PAP therapy administered to the patient at a higher rate and/or pressure than that of the patient's spontaneous breathing in the awake state. In the awake state, this may result in discomfort to the patient caused by a combination of high breathing rates and/or pressure administered by a ventilator and the desynchrony with the patient's own spontaneous efforts with the mechanical breaths administered by the ventilator. Therefore, constant settings for PAP therapy that is delivered throughout both awake and sleep states of a patient do not provide optimal ventilatory support: because of the discomfort experienced by the patient while awake, the user may be forced to set a low constant breathing rate and/or pressure that carries over into a sleep state where the patient would tolerate (and benefit from) a higher level of breathing rate and/or pressure.

Figure 10:
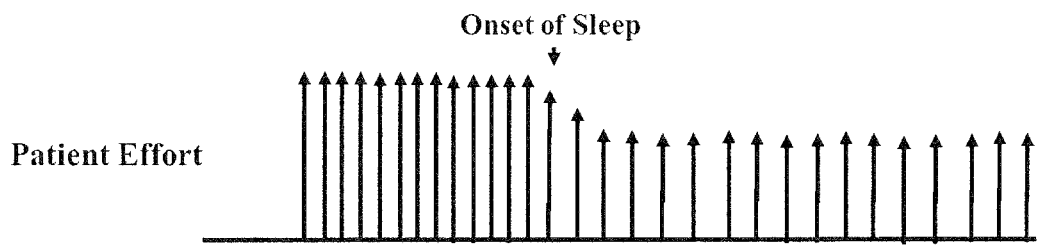
FIG. 10 shows an exemplary breathing pattern of a patient having hypoventilation upon onset of sleep.
Figure 11:
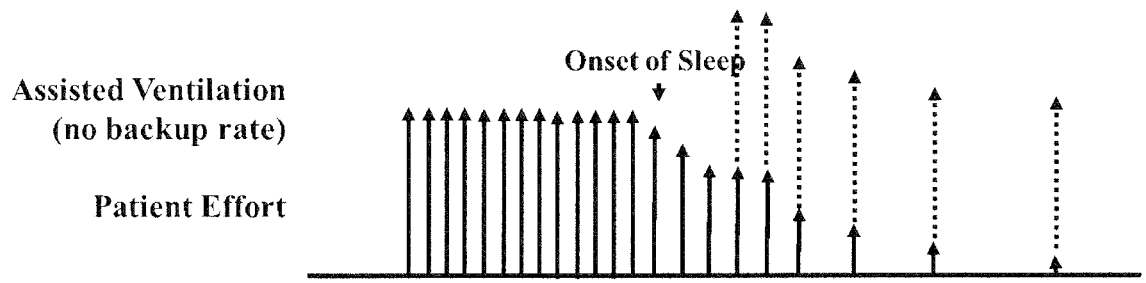
FIG. 11 shows an exemplary breathing pattern of a patient having hypoventilation upon onset of sleep administered with a short series of mechanical breaths.

FIG. 10 illustrates an exemplary breathing pattern of a patient experiencing hypoventilation upon onset of sleep. The solid lines represent the patient's own breathing efforts. The patient's spontaneous breathing and ventilation may increase when the patient is in an awake state, and decrease when the patient is in a sleep state. Therefore, if the patient experiences disruptions to sleep, this can also cause instability in the patient's breathing patterns. This disruption in sleep can mimic other oscillating SDB (as in CSR); however, the primary abnormality is insufficient breathing, which is exacerbated with sleep and wake alternation. Because the patient has a low spontaneous respiratory drive, when ventilatory support is administered while the patient is in a sleep state, it is believed that the patient's respiratory drive will continue to decrease and the patient may even cease to make any further breathing efforts, as shown in FIG. 11. The solid lines in FIG. 11 represent the patient's own breathing efforts and the dotted lines represent airflow administered by the initial series of mechanical breaths. Accordingly, the goal in treating patients with hypoventilation, particularly hypercapnic ventilation such as OHS, is to remedy the patient's insufficient breathing at a time during sleep when he will allow this, and enable the patient to breathe more than his low spontaneous respiratory drive.

Figure 12:
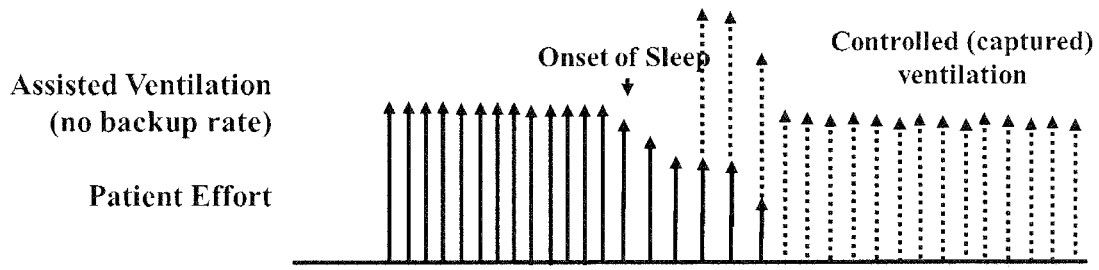
FIG. 12 shows an exemplary breathing pattern of a patient having hypoventilation upon onset of sleep administered with a short series of mechanical breaths and captured by a ventilatory system.

The loss of the patient's spontaneous respiratory drive, as shown in FIG. 11, may be counter-balanced by mechanically initiating breaths using a ventilatory system when the patient fails to spontaneously initiate his own breathing. In some embodiments, the mechanically initiated breaths may be a bi-level PAP therapy. If the patient in a sleep state ceases to make any further breathing efforts and relies on a ventilatory system 1 to initiate all breaths, the patient is referred to as having been "captured" by the system. An exemplary breathing pattern of a "captured" patient is shown in FIG. 12. The solid lines in FIG. 12 represent the patient's own breathing efforts and the dotted lines represent airflow administered by the system 1. By capturing the patient with the ventilatory system 1, it is believed that higher levels of breathing may be accomplished while the patient is in a sleep state, as compared to the breathing levels of the patient's own spontaneous breaths.

Figure 13:
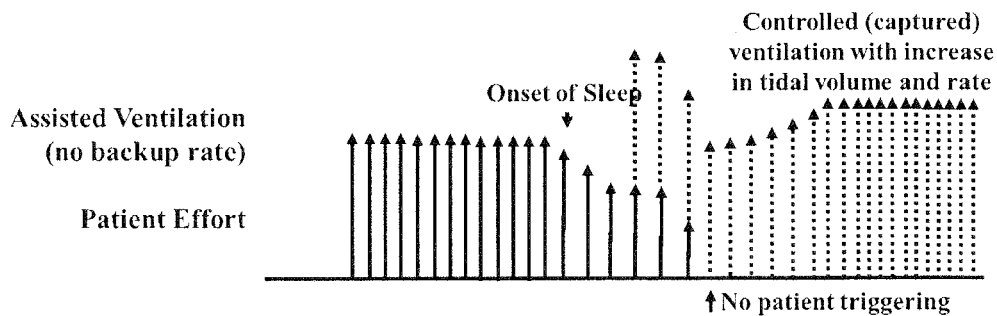
FIG. 13 shows an exemplary breathing pattern of a patient having hypoventilation upon onset of sleep captured by a ventilatory system delivering mechanical breaths having a rate greater than or equal to a spontaneous breathing pattern of the patient when the patient is in an awake state.

The methods 200 and 300 as described above deliver an initial series of mechanical breaths. It is believed that this initial series of mechanical breaths administered in step 208 or 308 will further decrease the patient's own spontaneous breathing by reflex and allow the system 1 to completely take over breathing for the patient during a sleep state. By taking over breathing for the patient during a sleep state, it is then possible to force the patient to breathe at a higher level than his own low spontaneous respiratory drive at a time he will allow this without discomfort (during sleep). For example, as shown in FIG. 13, the system 1 may deliver mechanical breaths at a higher level than the patient's own low spontaneous respiratory drive. The solid lines in FIG. 13 represent the patient's own breathing efforts and the dotted lines represent airflow administered by the system 1. As discussed above, such an increase in breathing levels may cause discomfort to the patient in an awake state.

The advantage of methods 200 and 300 for treatment of hypoventilation is that it does not require precise monitoring and detection of the patient's ventilation, but instead, relies on relative flow increases and/or decreases of patient's breathing to trigger administration of the initial series of mechanical breaths. In particular, a short-term drop in ventilation can be used to mark sleep onset, and resumption of triggered breaths or irregularity can indicate awakening and the need to stop therapy. For example, method 300 does not require precise detection of the patient's breathing patterns, but instead triggers step 308 upon detection of the patient's breathing level falling below a predetermined threshold value (step 306). It is believed that the reduction in monitoring and simplified (e.g., non-quantitative) detection of real-time breathing patterns provide a major improvement to treatment of hypoventilation, as such real-time measurements provide computationally complex challenges and accurate measurements are difficult to obtain.

Figure 14:
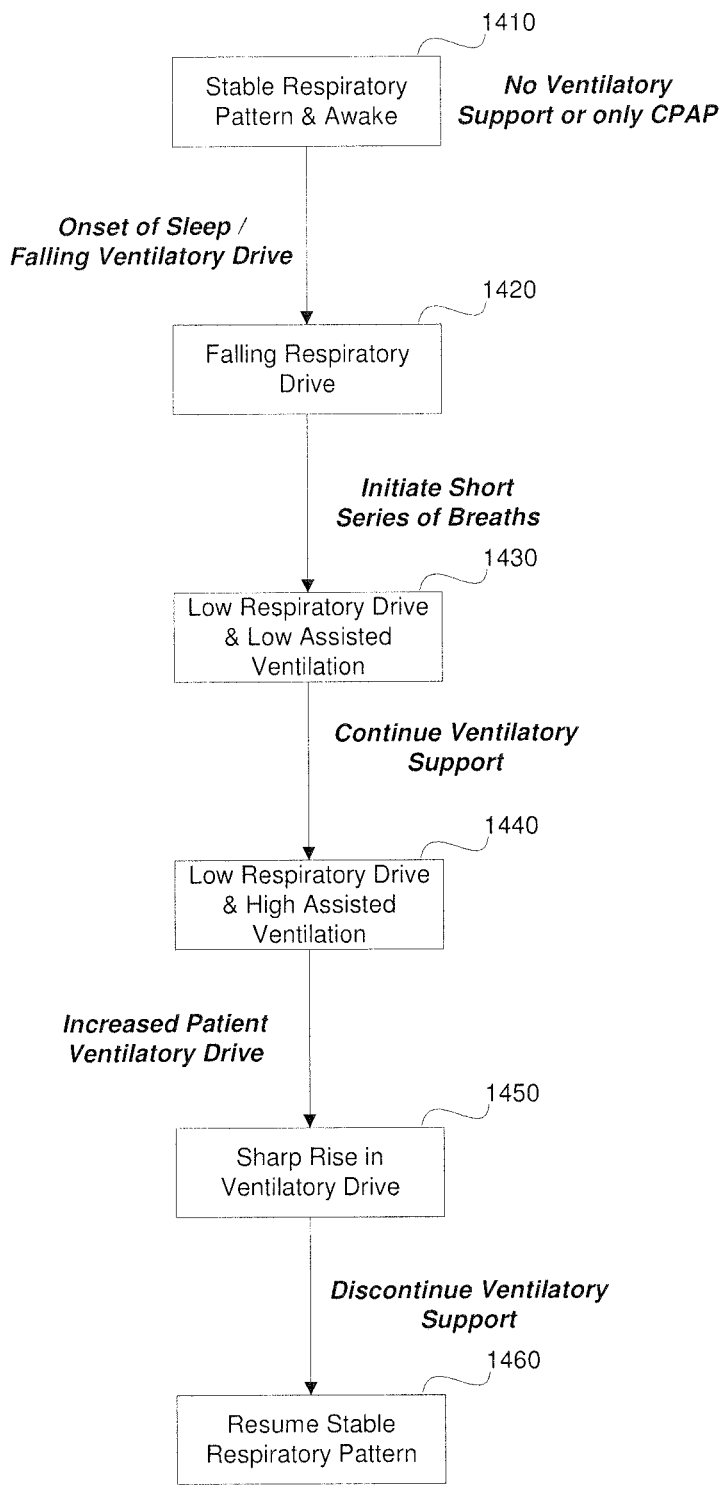
FIG. 14 an exemplary progression of breathing states for a patient having hypoventilation administered with a short series of mechanical breaths and captured by a ventilatory system.

FIG. 14 illustrates an exemplary progression of breathing states in a patient with hypoventilation, and as the patient's breathing is treated with ventilatory support in the manner described above in methods 200 and 300. In state 1410, the patient is awake and demonstrates a respiratory pattern with relatively high ventilatory drive, which may be stable and regular but often has additional irregularities. Typically, the patient in state 1410 has a high respiratory rate but experiences irregularities in breathing rate and tidal volume. As the patient falls asleep, the onset of sleep transitions the patient from state 910 to state 920. The patient in state 1410 typically does not receive any ventilatory support or may be administered with a baseline (CPAP). In state 1420, the patient may experience a falling respiratory drive. In patients suffering from hypoventilation, a decrease in the patient's ventilatory efforts may be particularly pronounced during onset of sleep. The patient in state 1420 typically experiences a falling respiratory rate and a falling respiratory drive.

Step 306, as described above, determines if the patient's breathing pattern has fallen below a predetermined threshold. It is believed that step 306 may be utilized to detect the patient's transition from state 1410 to state 1420 and thus, trigger ventilatory support for a hypoventilatory patient further losing respiratory drive. For example, the processing arrangement 24 may direct the flow generator 22 to administer an initial series of mechanical breaths to the patient, as described above in steps 208 and 308. It is believed that this initial series of mechanical breaths administered in step 208 or 308 further decreases the patient's own spontaneous respiratory drive and transitions the patient to state 1410. As the patient's own breathing efforts decrease, the methods 200 and 300 continue ventilatory support for the patient, for example, as described in step 212 or 312.

In state 1430, the patient may experience a decreased respiratory drive. Here, the patient is a sleep state (e.g., fully developed sleep or having REM sleep) and experiences low ventilation. Typically, the patient initiates few or no breaths spontaneously on his own. The processing arrangement 24 may direct the flow generator 22 to initially deliver breaths having a pressure, rate, frequency and/or tidal volume that corresponds to or is less than that provided by the patient's own spontaneous breathing in an awake state. Subsequently, the processing arrangement 24 may increase the level of breaths (e.g., higher pressure, rate, frequency and/or tidal volume) delivered to the patient, and preferably reach a level greater than that provided by the patient's own spontaneous breathing in an awake state. In some embodiments, the breaths may be increased incrementally. As the level of breaths increases, the patient transitions to state 1440, where the patient is "captured" by the system 1 and patient initiated respiration ceases. The system 1 continues to provide ventilatory support at the increased level to the patient in state 1440. In some embodiments, this is maintained only as long as the patient is passive (e.g., in a sleep state) or does not show the characteristic irregular breathing of wakefulness.

In one particular embodiment, the processing arrangement 24 may monitor the patient's breathing patterns to determine if the patient transitions from state 1440 to state 1450. In state 1450, the patient is no longer captured and demonstrates initial stages associated with a sharp rise in the patient's ventilatory drive. Generally, this change in breathing pattern signals awakening of the patient and/or the patient suffering from discomfort induced by the ventilator. More particularly, this rise in ventilatory drive is associated with a transition from a sleep state to an awake state, or from REM to Non-REM sleep. A patient in state 1450 resumes spontaneous breathing despite receiving ventilatory support, but may still experience irregular and large breathing patterns. As irregular breathing characteristic of wakefulness is detected, methods 200 and 300 stop providing airflow to the patient. It is believed that ceasing further ventilatory support to the patient in an awake state will allow the patient to resume to a respiratory pattern with relatively high ventilatory drive (state 1460).

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for treating hypercapnia, comprising the steps of:
    obtaining data corresponding to a spontaneous breathing pattern of a patient in an awake state;
    determining a spontaneous breathing characteristic corresponding to a spontaneous breathing rate associated with the spontaneous breathing pattern;
    monitoring a real-time breathing pattern of the patient;
    determining when the real-time breathing pattern of the patient falls below a predetermined threshold; and
    when the real-time breathing pattern falls below the predetermined threshold, continuously supplying an airflow to an airway of the patient at a rate selected to generate an altered breathing pattern corresponding to an altered breathing characteristic corresponding to an altered breathing rate, the altered breathing characteristic being, under predetermined conditions, greater than the spontaneous breathing characteristic.

2. The method of claim 1, wherein the predetermined threshold corresponds to a predetermined percentage of a baseline breathing pattern.

3. The method of claim 1, wherein the airflow is supplied to the airway in a first predetermined pattern corresponding to a mechanical breathing pattern at a mechanical breathing rate greater than the spontaneous breathing rate of the patient when the patient is in the awake state.

4. The method of claim 1, wherein the rate is predetermined independent of the breathing pattern of the patient.

5. The method of claim 1, wherein the airflow is supplied to the airway in a first predetermined pattern corresponding to a bi-level PAP having an inspiratory pressure and an expiratory pressure lower than the inspiratory pressure, wherein a differential between the expiratory and the inspiratory pressures is about 10 cm of $H_2O$ to about 25 cm of $H_2O$.

6. The method of claim 5, wherein the expiratory pressure is from 0 cm of $H_2O$ to about 15 cm of $H_2O$.

7. The method of claim 5, wherein the inspiratory pressure is from about 10 cm of $H_2O$ to about 30 cm of $H_2O$.

8. The method of treating hypercapnia of claim 1, further comprising the steps of:
    determining a state of wakefulness of the patient based on the breathing pattern; and
    discontinuing the supply of airflow to the airway of the patient when the state of wakefulness is an awake state.

9. The method of treating hypercapnia of claim 1, further comprising the steps of:
    determining a state of wakefulness of the patient based on the breathing pattern; and
    discontinuing the supply of airflow to the airway of the patient when the real-time breathing pattern corresponds to an irregular spontaneous breathing pattern corresponding to the awake state.

10. The method of claim 1, further comprising the steps of:
    determining a state of wakefulness of the patient based on the breathing pattern; and
    reducing the airflow to the airway of the patient when the state of wakefulness is the awake state.

11. The method of claim 10, wherein the reduced airflow is administered in a second predetermined pattern corresponding to a CPAP.

12. The method of claim 10, wherein the reduced airflow is administered in a second predetermined pattern corresponding to a bi-level PAP.

\* \* \* \* \*